US006232516B1

(12) United States Patent
van Beek et al.

(10) Patent No.: US 6,232,516 B1
(45) Date of Patent: *May 15, 2001

(54) PROCESS FOR CYCLOPENTADIENE SUBSTITUTION

(75) Inventors: Johannes A. M. van Beek, Mountain View, CA (US); Gerardus J. M. Gruter, Maastricht; Richard Green, Geleen, both of (NL)

(73) Assignee: DSM N.V., Heerlen (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/850,930

(22) Filed: May 2, 1997

Related U.S. Application Data

(60) Provisional application No. 60/024,991, filed on Sep. 3, 1996.

(30) Foreign Application Priority Data

May 3, 1996 (NL) .................................................. 1002998

(51) Int. Cl.[7] ..................................................... C07C 2/86
(52) U.S. Cl. ............................. 585/359; 585/375; 585/23
(58) Field of Search ..................................... 585/359, 375, 585/23

(56) References Cited

U.S. PATENT DOCUMENTS 3,255,267 * 6/1966 Fritz et al. ............................. 585/23
3,560,583 * 2/1971 Stewart ................................. 585/359
4,567,308 * 1/1986 Yoshida et al. ....................... 585/375
4,814,532 * 3/1989 Yoshida et al. ....................... 585/357
4,929,782 * 5/1990 Venier et al. ......................... 585/375
5,144,095 * 9/1992 Venier et al. ......................... 585/20

OTHER PUBLICATIONS

R. Allen Williams et al., 'Encapsulated Alkaline–Earth Metallocenes. Synthesis, Solution Behavior, and Solid–State Structures of . . . ', Journal of the American Chemical Society, vol. 113, No. 13, Jun. 19, 1991, pp. 4843–4851.

Clifford G. Venier et al., 'D–tert–butylcyclopentadiene and Tri–tert–butylclopentadiene', Journal of the American Chemical Society, vol. 112, No. 7, Mar. 28, 1990.

Eckehard V. Dehmlow et al., 'Phase Transfer Catalyzed tert–Alkylations of Cyclopentadiene and Indene: Indications of Set Processess', Tetrahedron Letters, vol. 32, No. 41, Oct. 1991.

* cited by examiner

*Primary Examiner*—Walter D. Griffin
(74) *Attorney, Agent, or Firm*—Pillsbury Winthrop LLP

(57) ABSTRACT

The process for the preparation of a selectively substituted cyclopentadiene compound which includes reacting a halide of a substituting compound in a mixture of the cyclopentadiene compound and an aqueous solution of a base in the presence of a phase transfer catalyst, wherein during the reaction the quantity of base relative to the cyclopentadiene compound may at any moment be between 5 and 30 mol/mol.

12 Claims, 1 Drawing Sheet

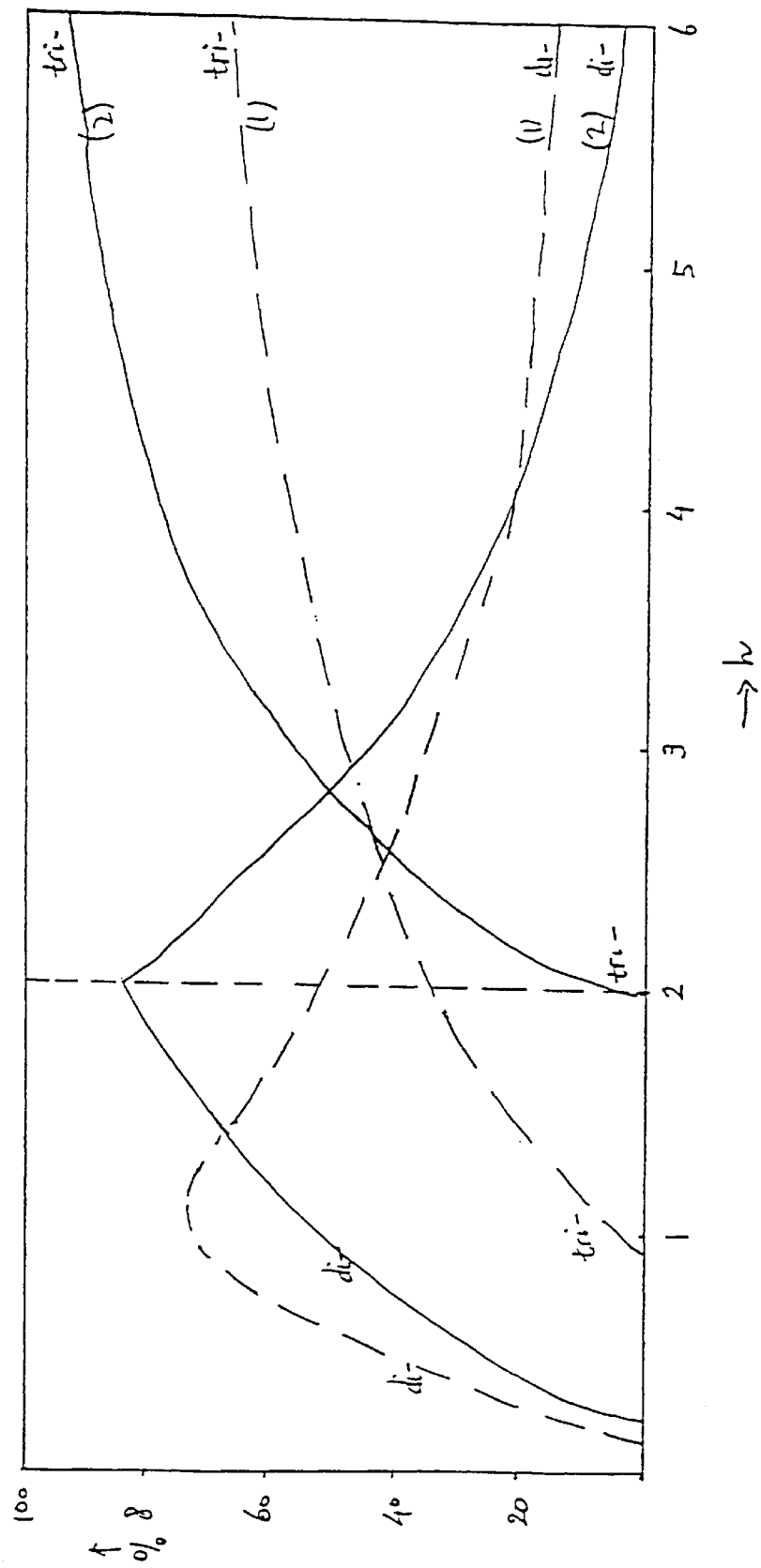

PROCESS FOR CYCLOPENTADIENE SUBSTITUTION

This application claims priority to application No. NL 1002998 filed on May 3, 1996 in the Netherlands and to provisional application 60/024,991 filed on Sep. 3, 1996, the complete disclosures of which are incorporated herein by reference.

BACKGROUND OF THE INVENTION

1. Field of the Invention

The invention relates to a process for the preparation of a substituted cyclopentadiene compound, and in particular to a process that permits excellent control over the selectivity of the substitutions on the resultant substituted cyclopentadiene compound. The substituted cyclopentadiene compound has utility as, for example, a ligand of a metal or transition metal complex used to catalyze a polymerization reaction.

2. Description of the Related Art

Substituted cyclopentadienes and their derivatives have utility as, for example, ligands in metal and transition metal complexes, which complexes can be used as catalysts in a polymerization reaction. The nature of the ligands, including the substituted cyclopentadienyl ligand, on the metal complexes can have a significant affect on the efficiency of the polymerization reaction and the characteristics (for example, average molecular weight) of the polymers prepared from the process. Accordingly, a process for preparing substituted cyclopentadienes in which the selectivity of the substituted cyclopentadienes produced can be meaningfully controlled would be of great benefit.

The preparation of a substituted cyclopentadiene compound is described by Williams et al., *J. Am. Chem. Soc.*, 113, 4843–4851, (1991) (hereinafter "Williams"), the complete disclosure of which is incorporated herein by reference, which details the preparation of isopropyl substituted cyclopentadiene by the reaction of a mixture of aqueous KOH, isopropyl bromide and cyclopentadiene in a molar ratio of 40:5:1, with ADOGEN 464 being used as a phase transfer catalyst. A drawback of this process is that a mixture of tri- and tetraisopropyl cyclopentadiene in a ratio of about 35:65 is obtained. This mixture has to then undergo a separate isolation step in order to obtain the individual compounds.

From Venier et al., *J. Am. Chem. Soc.*, 112, 2808–2809, (1990) (hereinafter "Venier"), the complete disclosure of which is incorporated herein by reference, it is known to prepare di-tert-butyl cyclopentadiene with a selectivity of 90%; however, such high selectivity appears to be the exceptional case, as seen by the remaining examples set forth in Williams. The high selectivity of the preparation of di-tert-butyl cyclopentadiene is primarily due to the fact that a tertiary alkyl, with a high degree of steric hindrance, is being substituted onto the cyclopentadiene ring. In such a case it is the low probability of obtaining the tri-tert-butylcyclopentadiene compound, with its high degree of steric hindrance, which is responsible for the high percentage of di-substituted compounds.

However, a selection mechanism based on the steric effects of the substituent will not be effective in the case of substituents which have less steric hindrance, for instance n- or sec-alkyl groups.

A need therefore exists for a synthetic route to produce substituted cyclopentadiene compounds, which process allows for improved selectivity, control and flexibility over the number and kind of substituents on the cyclopentadiene ring.

SUMMARY OF THE INVENTION

It is therefore an object of the present invention to provide a process for the preparation of substituted Cp compounds with a greater selectivity and control over the substitution than the known processes. In accordance with the principles of the present invention, this and other objects are achieved in that during the reaction, the ratio of base to Cp compound is maintained in a ratio of from about 5 to about 30 mol/mol.

With the process according to the present invention, it is possible to obtain substituted Cp compounds which have various and desirable degrees of substitution, and to produce those compounds at a higher selectivity than with the known process.

Accordingly, the process according to the present invention provides synthetic routes to a wide variety of substituted Cp and substituted Cp derivatives which can be utilized in catalyst preparation, and thus fills a clear, long-felt need.

As used herein, cyclopentadiene or "Cp" can refer to either an uncharged cyclopentadiene group or its derivative, or an anionic cyclopentadienyl group or its derivative, as those skilled in the art can determine the appropriate meaning based on the context in which the term is used. Examples of cyclopentadiene derivatives include substituted cyclopentadiene groups such as methyl cyclopentadiene.

These and other objects, features, and advantages of the present invention will become apparent from the accompanying drawing which illustrates, by way of example, the principles of the present invention.

BRIEF DESCRIPTION OF THE DRAWINGS

The drawing is a graph illustrating the concentrations of di- and tri-substituted isopropylcyclopentadiene versus reaction time for Example I.

DETAILED DESCRIPTION OF THE INVENTION

In accordance with an embodiment of the present invention, a process is provided for substituting one or more substituents onto a cyclopentadiene ring to thereby increase the number of substituents on the five-member ring. The process comprises reacting a compound comprising a cyclopentadiene ring with at least one first substituting compound comprising a first substituting group and a first halide to thereby substitute the first substituting group on the five-member ring defining the cyclopentadiene group. The reacting step takes place in a reaction mixture comprising at least one phase transfer catalyst, an organic phase and a first aqueous phase, and at least one first base, with a molar ratio of the first base to the compound comprising a cyclopentadiene ring in a range of from about 5 to about 30.

The process according to the present invention is directed to the conversion of unsubstituted Cp compounds to mono-substituted or multi-substituted compounds, and also to the further substitution of mono-substituted or multi-substituted Cp compounds. Where desired, the substitution step can optionally be followed by ring closure between ring substituents to form a second closed ring, thus producing compounds such as indene.

Depending on the size and the related degree of steric hindrance of the substituents, three- to six-fold substituted Cp compounds can be obtained. Primary and secondary alkyls, in general, can be substituted up to four-fold and even six-fold by the process according to the present invention under normal operating conditions (e.g., 1 to 10 bar, −20° C. to 120° C.). Tertiary butyl and other tertiary alkyls, such as 1, 1-dimethylbutyl, 1-methyl-1-ethylhexyl, 1,1-diethylpentyl and 1,1-diethylpropyl can be substituted up to three-fold under those normal operating conditions. Six-fold substitution would result in a geminal substitution onto a Cp-ring atom, since two substitutions would be present on one of the atoms defining the five-member Cp ring.

Suitable substituents include hydrocarbons, such as, for example, alkyl, alkenyl and aralkyl groups, as well as linear, branched and cyclic groups. Further, these hydrocarbons may also contain, besides carbon and hydrogen, one or more hetero atoms from groups 14–17 of the Periodic Table of Elements, (as published on the inside cover of the *CRC Handbook of Chemistry and Physics,* 73rd Edition, CRC Press (1992)). Suitable hetero atoms include, for instance O , N, Si or F.

The suitable alkyls can generally range from $C_1$ to $C_{20}$, more preferably from $C_1$ to $C_{10}$, such as, for instance, methyl, ethyl, n-propyl, (iso)propyl, secondary butyl, (tertiary) butyl and other homologues, pentyl, hexyl and octyl. The alkenyls can generally range from $C_2$ to $C_{20}$, more preferably from $C_2$ to $C_{10}$, such as, for instance, ethylene, (iso)propylene, secondary butylene, pentylene, hexylene and octylene. The alkyls can also be utilized in their cyclic forms, such as, for instance, cyclobutyl, cyclopentyl, cyclohexyl, cycloheptyl. Cycloalkenyls are also suitable, for instance, cyclohexenyl, cyclooctenyl, and cyclobutenyl. These cyclic groups can also have alkyl and alkenyl groups attached thereto, such as, for instance, ethylcyclohexenyl, methylcyclohexenyl and ethylcyclobutenyl. Aromatic hydrocarbons, including both aryl and aralkyl, are also suitable for substituting onto the Cp compound, such as, for instance, benzyl and ethylbenzyl.

For the process according to the present invention, the substituents are used in the form of their halides, preferably in the form of their bromides. When bromides are used it appears that a smaller amount of phase transfer catalyst suffices and that a greater yield of the desired compound is achieved.

A further advantage of the process according to the present invention is that a nearly stoichiometric amount of the substituting compound, can be used in the reaction process, so that in the final reaction mixture a smaller amount of non-reacted substituting compound remains. A stoichiometric amount means the molar amount which corresponds to the desired multiplicity of substitution, for instance, the molar ratio of substituting compound to Cp compound is 2 if two-fold substitution with the substituent is desired, 3 if a three-fold substitution is desired, and so on. For the purpose of comparison, reference is made to Williams, where 5 equivalents of isopropyl bromide were added in order to obtain a mixture of three- and four-fold substituted Cp compounds. In particular, if primary or secondary alkyl bromides are substituted, it is preferable to use these alkyl bromides in stoichiometric amounts or in a slight excess of stoichiometric amounts, but preferably not more than about 20% excess and more preferably not more than about 10% excess. This applies in particular to the case of substitution of tertiary alkyls or other voluminous substituents and to the case of substitution of the fourth, fifth, or sixth substituent on the same Cp molecule.

As a result of the high degree of selectivity of the process according to the present invention, Cp compounds which are substituted with specific desired combinations of substituents can be obtained without intermediate separation or purification. It is thus possible, for instance, first to effect a two-fold substitution by means of a certain halide, and then after that substitution reaction is complete, effecting, in the same reaction mixture, a third substitution by adding a second, different halide to the mixture after some time. This can be repeated, so that Cp derivatives with three or more different substituents can be obtained.

The process according to the present invention offers an improved selectivity with respect to the degree of substitution of the Cp compounds. If linear alkyls are being substituted onto the Cp ring, position isomers may form as a result of competition between 1,2- and 1,3-substitution. In the case of substitution with secondary or tertiary alkyls a second substituent will in general not be substituted in a position adjacent to the first substituent (position isomerism). Several double bonding isomers are formed per position isomer. When used as a ligand in a metal complex, the distinction between the double bond isomers does not play a significant role. Separation of those double bond isomers is therefore superfluous. The foregoing applies by analogy to triply substituted compounds. Geminal substitution of a second substituent onto a Cp ring carbon, which already has a substituent, may also occur. Geminally substituted Cp compounds can be easily separated, however, from non-geminally substituted compounds, because the latter can be converted to a Cp anion, in contrast to the former. All these forms of isomerism also occur in the Williams process, but the additional occurrence of varying degrees of substitution in that process makes isolation of the different reaction products much more difficult than in the process according to the present invention.

The substitution takes place in a mixture of the initial Cp compound and an aqueous solution of a base. The concentration of the base in the solution is preferably between about 20 wt. % and about 80 wt. %, more preferably between about 40 wt. % and about 60 wt. %. Concentrations of about 50 wt. % have been found to be most preferred.

By preference a hydroxide of an alkali metal, for instance K or Na, is used as the base. It has also been found that the use of NaOH instead of KOH, which is commonly used in the literature, results in a considerable increase in the rate of reaction. Thus, NaOH is preferably used as base in the process according to the present invention. It has appeared that a substantial reduction of the reaction time can be achieved if the basic solution is refreshed during the reaction, for instance by first mixing the basic solution with the other components of the reaction mixture and after some time isolating the aqueous phase from the reaction mixture and replacing it with a fresh portion of basic solution.

The effect of replacing the aqueous basic solution with a fresh portion of basic solution is illustrated in the drawing. As further detailed under the Example section, in reaction 2, the solid line in the FIGURE, the basic solution was removed after 2 hours with the di-substituted compound present at a 85% level and virtually none of the tri-substituted compound present. The addition of the fresh basic solution apparently triggers the addition of the third substituent onto the di-substituted Cp compound. In contrast, in reaction 1, the dashed line in the figure, in which the amount of the basic solution was double that of reaction 2, formation of the tri-substituted Cp compound was first observed when the level of the di-substituted compound was only 70%. Thus with the higher amount of the basic solution, the process of substituting groups onto Cp compounds appears to be less selective and results in a mixture of Cp compounds with varying numbers of substituents.

Generally, the base is present in an amount of about 5 to about 30 mol per mole of Cp compound, preferably in an amount of about 6 to about 20, more preferably in an amount of about 7 to about 15 mol per mole of Cp compound. These quantities are significantly lower than the amount of 40 mol per mole of Cp compound reported in the literature.

The substitution takes place at atmospheric or elevated pressure, for instance up to about 100 MPa, which higher level is applied in particular if volatile components are present. The temperature at which the reaction takes place may vary within wide limits, for instance from about 20° C. to about 120° C., preferably between about 10° C. and about 50° C. Starting up the reaction at room temperature is usually the preferred step, after which the temperature of the reaction mixture can increase due to the exothermic nature of the reactions.

The substitution takes place in the presence of a phase transfer catalyst which transfers hydroxide ions from the aqueous phase to the organic phase which contains the Cp compound and the organic halide. The hydroxide ions react in the organic phase with a hydrogen atom which can be extracted from the Cp compound. In principle, suitable phase transfer catalysts are quaternary ammonium, phosphonium, arsonium, antimonium, bismuthonium, and tertiary sulfonium salts. More preferably, ammonium and phosphonium salts are used, for example tricaprylmethylammonium chloride, commercially available under the name ALIQUAT 336 (Fluka AG, Switzerland; General Mills Co., USA) and ADOGEN 464 (Aldrich Chemical Co., USA). Compounds such as, for example, benzyltriethylammonium chloride (TEBA) or benzyltriethylammonium bromide (TEBA-Br), benzyltrimethylammonium chloride, benzyltrimethylammonium bromide or benzyltrimethylammonium hydroxide (TRITON B), tetra-n-butylammonium chloride, tetra-n-butylammonium bromide, tetra-n-butylammonium iodide, tetra-n-butylammonium hydrogen sulphate or tetra-n-butylammonium hydroxide and cetyltrimethylammonium bromide or cetyltrimethylammonium chloride, benzyltributyl-, tetra-n-pentyl-, tetra-n-hexyl- and trioctylpropylammonium chlorides and their bromides are likewise suitable. Usable phosphonium salts include, for example, tributylhexadecylphosphonium bromide, ethyltriphenylphosphonium bromide, tetraphenylphosphonium chloride, benzyltriphenylphosphonium iodide and tetrabutylphosphonium chloride. Crown ethers and cryptands can also be used as the phase transfer catalyst, for example, 15-crown-5, 18-crown-6, dibenzo-18-crown-6, dicyclohexano-18-crown-6, 4,7,13,16,21-pentaoxa-1,10-diazabicyclo[8.8.5]ricosane (KRYPTOFIX 221), 4,7,13,18-tetraoxa-1,10-diazabicyclo[8.5.5]eicosane (KRYPTOFIX 211) and 4,7,13,16,21,24-hexaoxa-1,10-diazabicyclo[8.8.8]-hexacosane ("[2.2.2]") and its benzo derivative (KRYPTOFIX 222 B). Polyethers such as ethers of ethylene glycols can also be used as the phase transfer catalyst. Quaternary ammonium salts, phosphonium salts, phosphoric acid triamides, crown ethers, polyethers and cryptands can also be used on supports such as, for example, on a crosslinked polystyrene or another polymer. The phase transfer catalyst is used in an amount of about 0.01 to about 2 equivalents, preferably about 0.05 to about 1 equivalents on the basis of the amount of Cp.

The sequence of addition of the various components to the reactor generally is not essential in the implementation of the process. A suitable procedure is first to add basic solution, catalyst and Cp compound and then, after thorough stirring, the halide. It is also possible to first add and thoroughly stir the halide, the Cp compound and the catalyst and then add the basic solution. In all the embodiments described it is found that a considerable shortening of the reaction time can be achieved if the basic solution is applied in portions, for instance by isolating and removing the aqueous basic phase from the reaction mixture and replacing it by a fresh portion of the basic solution. This appears to be advantageous in particular when a tri- or tetrasubstitution is carried out. A further advantage of intermediate refreshing of the aqueous phase, besides the shortening of the reaction time, is that a much smaller reaction volume results. This advantage is also achieved owing to the amount of aqueous phase being much smaller than in the process according to the state of the art. Optionally, at the same time when the basic solution is replaced a second desired substituent in halogenated form can be added in order to obtain a Cp compound substituted with different substituents as described in the foregoing. Examples XII and XXIV illustrate the process according to the present invention as utilized to synthesize Cp compounds with different substitutents.

The timing of replacement of the aqueous basic solution and/or addition of any second halide can be determined by monitoring the reaction with gas chromatography. The observed decrease of the rate of reaction determines the timing of replacement of the basic solution. The timing of the addition of a second halide can also be determined by GC monitoring. The order of addition of the substituting compounds may influence the identity of the position isomers which are obtained.

Upon completion of the reaction the aqueous phase and the organic phase containing the substituted Cp compound are separated. Any collected aqueous phases are discarded in the appropriate environmentally correct manner. Next, the substituted Cp compound is recovered from the organic phase by fractional distillation.

The process for cyclopentadiene is described in patent application number NL 1002998 filed on May 3, 1996 in the Netherlands, the complete disclosure of which is incorporated herein by reference.

The invention will be further explained with reference to the following non-limiting examples. All manipulations of air-sensitive compounds were performed with standard high-vacuum, Schlenk, or drybox techniques.

The following analytical methods were used for characterization: Gas chromatography (GC) was carried out on a Hewlett-Packard 5890 series II with an HP crosslinked methyl silicon gum column (25 m×0.32 mm×1.05 $\mu$m). Combined gas chromatography/mass spectrometry (GC-MS) was carried out with a Fisons MD800 equipped with a quadrupole mass detector, auto injector Fisons AS800 and CPSil8 column (30 m×0.25×mm×1 $\mu$m, low bleed). NMR was carried out on either a Bruker ACP200 ($^1$H=200 MHz; $^{13}$C=50 MHz) or a Bruker ARX400 ($^1$H=400 MHz; $^{13}$C=100 MHz). To characterize metal complexes, use was made of a Kratos MS80 or alternatively a Finnigan Mat 4610 mass spectrometer.

EXAMPLES

Example I

Two reactions carried out with the process according to the invention were monitored over time using gas chromatography. The results are presented in the drawing. The percentages (%) of di- and tricyclopentadiene compounds formed relative to the total of cyclopentadiene compounds are plotted against the reaction time (h) for both reactions in the drawing. In reaction 1 (dashed curves in FIG. 1) the process according to the invention was carried out with a certain amount of cyclopentadiene, 3 equivalents of isopropylbromide and 10 mol% of ALIQUAT in 20 equivalents of 50 wt. % sodium hydroxide in water. In reaction 2 (solid curves in the figure) the ratio between the reactants was: 1 equivalent of cyclopentadiene to 3 equivalents of isopropylbromide to 10 mol % of ALIQUAT in 10 equivalents of sodium hydroxide (50 wt. %). In this case, in deviation from reaction 1, stirring was stopped after 2 hours and after phase separation, the aqueous layer was drawn off, and another 10 equivalents of sodium hydroxide (50 wt. % in water) were added. The reaction was then stirred for another 4 hours. The total number of equivalents of NaOH used in the two reactions were the same.

The drawing illustrates the differences that occurred in the reaction paths of the two reactions. In reaction 1 a mixture of di- and triisopropylcyclopentadiene in a ratio of about 21:68 is present after 6 hours' stirring. It is expected that when stirring is continued the amount of diisopropylcyclopentadiene will decrease and the amount of triisopropylcyclopentadiene will increase correspondingly. In reaction 2 both absolutely and relatively much more triisopropylcyclopentadiene is present after 6 hours stirring. The ratio between tri- and diisopropylcyclopentadiene is 93:4 in this case.

The drawing also shows the higher selectivity for the reaction with a lower concentration of base (reaction 2). After 2 hours there is virtually no triisopropylcyclopentadiene present in reaction 2, while at that moment already 85% of diisopropyl-cyclopentadiene has formed. In reaction 1 triisopropylcyclopentadiene is already forming with only 70% of diisopropylcyclopentadiene having formed. This shows the favorable effect of lowering the concentration of hydroxide on the selectivity towards the number of substituted groups. It may be observed that from the trend of the solid curve it is very likely that the amount of diisopropylcyclopentadiene will further increase if the reaction is allowed to continue. However in this example the basic solution was replaced after 2 hours with a fresh basic solution and the increase in the concentration of di-substituted Cp turns into an abrupt decline. It appears that the replacement of the basic solution triggers the formation of triisopropylcyclopentadiene. Therefore by appropriate timing of replacement of the aqueous basic layer both the reaction rate and the nature of the reaction product can be influenced. In reaction 1 as well as in reaction 2 triisopropylcyclopentadiene is ultimately obtained with a higher selectivity than the literature process, which utilizes 40 equivalents of hydroxide.

Example II

Preparation of di(2-propyl)cyclopentadiene

A 200 ml double-walled reactor, provided with baffles, condenser, top stirrer, thermometer and dropping funnel was charged with 180 g of 50 wt. % NaOH (2.25 mol), 9.5 g of ALIQUAT 336 (23 mmol) and 15 g (0.227 mol) of freshly cracked cyclopentadiene. The reaction mixture was stirred turbulently for a few minutes at a speed of 1385 rpm. Then 56 g of 2-propyl bromide (0.45 mol) were added, cooling with water taking place at the same time. A few minutes after the addition of the 2-propyl bromide the temperature rose by about 10° C. This was followed by stirring at 50° C. for 6 hours. GC was used to show that after 6 hours 92% of di(2-propyl)cyclopentadiene was present in the mixture of di- and tri(2-propyl)cyclopentadiene. The product was distilled at 10 mbar and 70°C. After distillation, 25.35 g of di(2-propyl)cyclopentadiene were obtained. Characterization took place with the aid of GC, GC-MS, $^{13}$C- and $^{1}$H-NMR.

Example III

Preparation of tri(2-propyl) cyclopentadiene

A 200 ml double-walled reactor, provided with baffles, condenser, top stirrer, thermometer and dropping funnel was charged with 180 g (2.25 mol) of 50 wt. % NaOH, 9.5 g of ALIQUAT 336 (23 mmol) and 15 g (0.227 mol) of freshly cracked cyclopentadiene were added. The reaction mixture was stirred turbulently for a few minutes at a speed of 1385 rpm. Then 84 g of 2-propyl bromide (0.68 mol) were added with simultaneous cooling with water. A few minutes after the addition of the 2-propyl bromide the temperature rose by about 10° C. GC was used to show that about 30 minutes after all 2-propyl bromide had been added, (monosubstituted) 2-propylcyclopentadiene had formed. Then the mixture was heated and stirred at 50° C. for 2 hours. The stirring and heating were stopped and the phases separated. The aqueous layer was drawn off and 180 g (2.25 mol) of fresh 50% NaOH were added, followed by stirring for 1 hour at 50° C. GC was used to show that after 1 hour the mixture of di-, tri and tetracyclopentadiene contained 90% to 95% of tri-(2-propyl) cyclopentadiene. The product was distilled at 1.3 mbar and 77° C. to 78° C.

After distillation, 31.9 g of tri-(2-propyl)cyclopentadiene were obtained. Characterization took place with the aid of GC, GC-MS, $^{13}$C- and $^{1}$H-NMR.

Example IV

Preparation of tetra(2-propyl)cyclopentadiene

Analogously to Example III, 114 g of 2-propyl bromide (0.93 mol) was added and the aqueous layer was replaced for a second time after 7 hours and at the same time another 5 g (12 mmol) of ALIQUAT 336 were added. Then heating for 16 hours at 55° C. took place. GC showed that after heating 85% of tetra(2-propyl)cyclopentadiene was present in the mixture of tri and tetracyclopentadiene. The product was distilled at 1.0 mbar and 88° C. to 90° C. After distillation, 34.9 g of tetra(2-propyl)cyclopentadiene were obtained. Characterization took place with the aid of GC, GC-MS, $^{13}$C- and $^{1}$H-NMR.

Example V

Preparation of di(cyclohexyl)cyclopentadiene

A 1 L double-walled reactor, provided with baffles, condenser, top stirrer, thermometer and dropping funnel was charged with 600 g of 50 wt. % NaOH (7.5 mol), followed by cooling to 8° C. Then 20 g of ALIQUAT 336 (49 mmol) and 33 g (0.5 mol) of freshly cracked cyclopentadiene were added. The reaction mixture was stirred turbulently for a few minutes. Then 172 g of cyclohexyl bromide (1.05 mol) were added, cooling with water taking place at the same time. After stirring for 2 hours at room temperature the reaction mixture was heated and stirred at 70° C. for 6 hours. GC was used to show that after that step 79% of di(cyclohexyl) cyclopentadiene were present. The product was distilled at 0.04 mbar and 110° C. to 120° C. After distillation, 73.6 g of di(cyclohexyl)cyclopentadiene were obtained. Characterization took place with the aid of GC, GC-MS, $^{13}$C and $^{1}$H-NMR.

Example VI

Preparation of tri(cyclohexyl)cyclopentadiene

A 1 L double-walled reactor, provided with baffles, condenser, top stirrer, thermometer and dropping funnel was charged with 600 g of 50 wt. % NaOH (7.5 mol), followed by cooling to 8° C. Then 20 g of ALIQUAT 336 (49 mmol) and 33 g (0.5 mol) of freshly cracked cyclopentadiene were added. The reaction mixture was stirred turbulently for a few minutes. Then 256 g of cyclohexyl bromide (1.57 mol) were added, cooling with water taking place at the same time. After stirring for 1 hour at room temperature the reaction mixture was heated and stirred at 70° C. for 2 hours. After 2 hours the mixture was allowed to cool to room temperature and then phases were separated. The aqueous layer was drawn off and 600 g (7.5 mol) of fresh 50 wt. % NaOH were added, followed by further stirring for 4 hours at 70° C. GC was used to show that after 4 hours 10% di- and 90% tri(cyclohexyl)-cyclopentadiene were present in the mixture. The product was distilled at 0.04 mbar and 130° C. After distillation, 87.4 g of tri(cyclohexyl)cyclopentadiene were obtained. Characterization took place with the aid of GC, GC-MS, $^{13}$C and $^1$H-NMR.

Example VII
Preparation of tetra(ethyl)cyclopentadiene

A 1 L double-walled reactor, provided with baffles, condenser, top stirrer, thermometer and dropping funnel was charged with 1050 g of 50 wt. % NaOH (13.1 mol), followed by cooling to 10° C. Then 32 g of ALIQUAT 336 (79 mmol) and 51 g (0.77 mol) of freshly cracked cyclopentadiene were added. The reaction mixture was stirred turbulently for a few minutes. Then 344 g of ethyl bromide (3.19 mol) were added gradually in one hour, cooling with water taking place at the same time. After 1 hour of stirring at room temperature the reaction mixture was heated to 35° C., followed by a further 6 hours of stirring. Stirring was stopped and phase separation was awaited. The aqueous layer was drawn off and 1050 g (13.1 mol) of fresh 50 wt. % NaOH were added, followed by a further 5 hour of stirring at room temperature. GC was used to show that after 5 hours 15% tri-, 78% tetra and 7% of penta(ethyl)cyclopentadiene were present in the mixture. The product was distilled at 11 mbar and 91° C. After distillation, 74.8 g of tetra(ethyl)-cyclopentadiene were obtained. Characterization took place with the aid of GC, GC-MS, $^{13}$C- and $^1$H-NMR.

Example VIII
Preparation of di(2-butyl)cyclopentadiene

A 1 L double-walled reactor, provided with baffles, condenser, top stirrer, thermometer and dropping funnel was charged with 600 g of 50 wt. % NaOH (7.5 mol), followed by cooling to 10° C. Then 30 g of ALIQUAT 336 (74 mmol) and 48.2 g (0.73 mol) of freshly cracked cyclopentadiene were added. The reaction mixture was stirred turbulently for a few minutes. Then 200 g of 2-butyl bromide (1.46 mol) were added gradually in half an hour, cooling with water taking place at the same time. After 2 hours of stirring at room temperature the reaction mixture was heated to 60° C., followed by a further 4 hours of stirring. GC was used to show that after 4 hours greater than 90% of di(2-butyl) cyclopentadiene was present in the mixture. The product was distilled at 20 mbar and 80° C. to 90° C. After distillation, 90.8 g of di(2-butyl)cyclopentadiene were obtained. Characterization took place with the aid of GC, GC-MS, $^{13}$C- and $^1$H-NMR.

Example IX
Preparation of tri(2-butyl)cyclopentadiene

A 1 L double-walled reactor, provided with baffles, condenser, top stirrer, thermometer and dropping funnel was charged with 400 g of 50 wt. % NaOH (5 mol). Then 9.6 g of ALIQUAT 336 (24 mmol) and 15.2 g (0.23 mol) of freshly cracked cyclopentadiene were added. The reaction mixture was stirred turbulently for a few minutes. Then 99.8 g of 2-butyl bromide (0.73 mol) were added in half an hour, cooling with water taking place at the same time. After half an hour of stirring at room temperature the reaction mixture was heated to 70° C., followed by a further 3 hours of stirring. Stirring was stopped and phase separation was awaited. The aqueous layer was drawn off and 400 g (5.0 mol) of fresh 50 wt. % NaOH were added, followed by a further 2 hours of stirring at 70° C. GC was used to show after 2 hours greater than 90% of tri(2-butyl) cyclopentadiene was present in the mixture of di, tri- and tetra(2-butyl)cyclopentadiene. The product was distilled at 1 mbar and 91° C. After distillation, 40.9 g of tri(2-butyl) cyclopentadiene were obtained. Characterization took place with the aid of GC, GC-MS, $^{13}$C- and $^1$H-NMR.

Example X
Preparation of di- and tri(2-pentyl)cyclopentadiene

A 1 L double-walled reactor, provided with baffles, condenser, top stirrer, thermometer and dropping funnel was charged with 900 g (11.25 mol) of 50 wt. % NaOH. Then 31 g of ALIQUAT 336 (77 mmol) and 26.8 g (0.41 mol) of freshly cracked cyclopentadiene were added. The reaction mixture was stirred turbulently for a few minutes. Then 155 g of 2-pentyl bromide (1.03 mol) were added over a period of 1 hour, cooling with water taking place at the same time. After 3 hours of stirring at room temperature the reaction mixture was heated to 70° C., followed by a further 2 hours of stirring. Stirring was stopped and phase separation was awaited. The aqueous layer was drawn off and 900 g (11.25 mol) of fresh 50 wt. % NaOH were added, followed by a further two hours of stirring at 70° C. GC was used to show that after 2 hours the mixture consisted of di- and tri(2-pentyl)cyclopentadiene (approximately 1:1). The products were distilled at 2 mbar, 79° C. to 81° C. and 0.5 mbar, 102° C., respectively. After distillation, 28 g of di- and 40 g of tri(2-pentyl)cyclopentadiene were obtained. Characterization took place with the aid of GC, GC-MS, $^{13}$C- and $^1$H-NMR.

Example XI
Preparation of di- and tri(3-pentyl)cyclopentadiene

A 1 L double-walled reactor, provided with baffles, condenser, top stirrer, thermometer and dropping funnel was charged with 430 g (5.4 mol) of 50 wt. % NaOH. Then 23 g of ALIQUAT 336 (57 mmol) and 27 g (0.41 mol) of freshly cracked cyclopentadiene were added. The reaction mixture was stirred turbulently for a few minutes. Then 150 g of 3-pentyl bromide (1.0 mol) were added over a period of 1 hour, cooling with water taking place at the same time. After 1 hour of stirring at room temperature the reaction mixture was heated to 70° C., followed by a further 3 hours of stirring. Stirring was stopped and phase separation was awaited. The aqueous layer was drawn off and 540 g (6.70 mol) of fresh 50 wt. % NaOH were added, followed by a further four hours of stirring at 70° C. GC was used to show that after 4 hours the mixture consisted of di- and tri(3-pentyl)-cyclopentadiene (approximately 3:2). The products were distilled at 0.2 mbar, 51° C. and 0.2 mbar, 77° C. to 80° C., respectively. After distillation, 32 g of di and 18 g of tri(3-pentyl)cyclopentadiene were obtained. Characterization took place with the aid of GC, GC-MS, $^{13}$C- and $^1$H-NMR.

Example XII
Preparation of di(2-propyl)cyclohexylcyclopentadiene

In a 200 mL double-walled reactor, provided with baffles, condenser, top stirrer, thermometer and dropping funnel, 150 g of 50 wt. % NaOH (1.9 mol), 7 g of ALIQUAT 336 (17.3 mmol) and 8.5 g (0.13 mol) of freshly cracked cyclopentadiene were combined. The reaction mixture was stirred turbulently at a speed of 1385 rpm for a few minutes. Then 31.5 g of 2-propyl bromide (0.26 mol) were metered in over 1 hour, cooling with water taking place at the same time. After addition of the bromide the reaction mixture was heated to 50° C. After 2 hours, stirring was stopped and phase separation was awaited. The aqueous layer was drawn off, and 150 g (1.9 mol) of fresh 50 wt. % NaOH were added. This was followed by the addition of 20.9 g (0.13 mol) of cyclohexyl bromide, and stirring was then continued for a further 3 hours at 70° C. GC was used to show that after 3 hours 80% of di(2-propyl)cyclo-hexylcyclopentadiene was present in the mixture. The product was distilled at 0.3 mbar and 80° C. After distillation, 17.8 g of di(2-propyl) cyclohexylcyclopentadiene were obtained. Characterization took place with the aid of GC, GC-MS, $^{13}$C- and $^1$H-NMR.

Example XIII

Preparation of tetra(octyl)cyclopentadiene

A 1.5 L double-walled reactor, provided with baffles, condenser, top stirrer, thermometer and dropping funnel was charged with 900 g of 50 wt. % NaOH (11.3 mol), followed by cooling to 10° C. Then 30 g of ALIQUAT 336 (74 mmol) and 48 g (0.72 mol) of freshly cracked cyclopentadiene were added. The reaction mixture was stirred turbulently for a few minutes. Then 577 g of octyl bromide (2.99 mol) were added in one hour, cooling with water taking place at the same time. After 1 hour of stirring at room temperature the reaction mixture was heated to 35° C., followed by a further 6 hours of stirring. Stirring was stopped and phase separation was awaited. The aqueous layer was drawn off and 920 g (11.5 mol) of fresh 50 wt. % NaOH were added, followed by a further 5 hours of stirring at room temperature. GC was used to show that after 5 hours 10% of tri-, 83% of tetra- and 7% of penta(octyl)cyclopentadiene were present in the mixture. The product was distilled at reduced pressure. After vacuum distillation, 226.6 g of tetra(octyl)cyclopentadiene were obtained. Characterization of the product took place with the aid of GC, GC-MS, $^{13}$C- and $^1$H-NMR.

Example XIV

Preparation of tetra(n-propyl)cyclopentadiene

A 1 L double-walled reactor, provided with baffles, condenser, top stirrer, thermometer and dropping funnel was charged with 1000 g of 50 wt. % NaOH (12.5 mol), followed by cooling to 10° C. Then 30 g of ALIQUAT 336 (74 mmol) and 50 g (0.75 mol) of freshly cracked cyclopentadiene were added. The reaction mixture was stirred turbulently for a few minutes. Then 373 g of propyl bromide (3.03 mol) were added in one hour, cooling with water taking place at the same time. After 1 hour of stirring at room temperature the reaction mixture was heated to 35° C., followed by a further 6 hours of stirring. Stirring was stopped and phase separation was awaited. The aqueous layer was drawn off and 990 g (12.4 mol) of fresh 50 wt. % NaOH were added, followed by a further 5 hours of stirring at room temperature. GC was used to show that after 5 hours 14% of tri-, 80% of tetra- and 6% of penta(propyl)cyclopentadiene were present in the mixture. The product was distilled at reduced pressure. After vacuum distillation, 103.1 g of 5 tetra(propyl)-cyclopentadiene were obtained. Characterization of the product took place with the aid of GC, GC-MS, $^{13}$C- and $^1$H-NMR.

Example XV

Preparation of tetra(n-propyl)cyclopentadiene

A 1.0 L double-walled reactor, provided with baffles, condenser, top stirrer, thermometer and dropping funnel equipped with a nitrogen inlet was charged with ALIQUAT 336 (7.03 g, 17 mmol) and 151 g of 50 wt. % NaOH aqueous solution. A cold (−10° C.) mixture of n-propylbromide (95.54 g, 0.78 mol) and freshly cracked cyclopentadiene (11.7 g, 0.18 mol) was then added via the dropping funnel to the turbulently stirred reaction mixture. The reaction mixture was cooled with water during the addition of the reactant. After 2 hours, stirring was stopped and the phases separated, the aqueous basic solution was isolated, removed and replaced with 144 g of a fresh 50 wt. % NaOH solution. After 3.5 more hours of stirring at room temperature, GC analysis showed that 18% of tri- and 82% of tetra-(n-propyl) cyclopentadiene were present in the mixture. The product was distilled at reduced pressure and after vacuum distillation, 29.6 g of tetra(n-propyl)cyclopentadiene were obtained. Characterization of the product took place with the aid of GC, GC-MS, $^{13}$C- and $^1$H-NMR.

Example XVI

Preparation of di(allyl)cyclopentadiene

A 1.0 L double-walled reactor, provided with baffles, condenser, top stirrer, thermometer and dropping funnel equipped with a nitrogen inlet was charged with ALIQUAT 336 (7.7 g, 19 mmol), allylbromide (43.6 g, 0.36 mol) and freshly cracked cyclopentadiene (11.9 g, 0.18 mol). A 50 wt. % NaOH aqueous solution (147 g) was then added via the dropping funnel to the turbulently stirred reaction mixture. The reaction mixture was cooled with water during the addition of the base. After 3 hours of stirring at room temperature, GC analysis showed that 6% of mono-, 75% of di- and 19% of tri(allyl)cyclopentadiene were present in the mixture. The product was distilled at reduced pressure and after vacuum distillation, 9.75 g of di(allyl)cyclopentadiene were obtained. Characterization of the product took place with the aid of GC, GC-MS, $^{13}$C- and $^1$H-NMR.

Example XVII

Preparation of tetra(allyl)cyclopentadiene

A 1.0 L double-walled reactor, provided with baffles, condenser, top stirrer, thermometer and dropping funnel equipped with a nitrogen inlet was charged with ALIQUAT 336 (8.0 g, 20 mmol), allylbromide (89.2 g, 0.74 mol) and freshly cracked cyclopentadiene (11.9 g, 0.18 mol). A 50 wt. % NaOH aqueous solution (149 g) was then added via the dropping funnel to the turbulently stirred reaction mixture. The reaction mixture was cooled with water during the addition of the base. After 3 hours, stirring was stopped and the phases separated, the aqueous basic solution was isolated, removed and replaced with a fresh 50 wt. % NaOH solution (149 g). After 2.5 hours of stirring at room temperature, stirring was stopped, the layers separated and product was distilled at reduced pressure. After vacuum distillation, 15.47 g of tetra(allyl)cyclopentadiene were obtained.

Characterization of the product took place with the aid of GC, GC-MS, $^{13}$C- and $^1$H-NMR.

Example XVIII

Preparation of tetra(4-butenyl)cyclopentadiene

A 1.0 L double-walled reactor, provided with baffles, condenser, top stirrer, thermometer and dropping funnel equipped with a nitrogen inlet was charged with ALIQUAT 336 (8.0 g, 20 mmol), 1-bromo-4-butene (97.6 g, 0.72 mol) and freshly cracked cyclopentadiene (11.9 g, 0.18 mol). A 50 wt. % NaOH aqueous solution (147 g) was then added via the dropping funnel to the turbulently stirred reaction mixture. After 2.5 hours the reaction mixture was heated to 30° C., then after another hour the stirring was stopped and the phases separated, the aqueous basic solution was isolated, removed and replaced with a fresh 50 wt. % NaOH solution (149 g) and the reaction mixture heated to 50° C. After 2 more hours the stirring was stopped and the phases separated, the aqueous basic solution was isolated, removed and replaced with a fresh 50 wt. % NaOH solution (149 g) and the reaction mixture heated to 60° C. After an hour of stirring at 60° C., the stirring was stopped, the layers separated and the product was distilled at reduced pressure. After vacuum distillation, 23.82 g of tetra(4-butenyl)cyclopentadiene were obtained. Characterization of the product took place with the aid of GC, GC-MS, $^{13}$C- and $^1$H-NMR.

Example XIX
Preparation of di(3-methyl-2-butenyl)cyclopentadiene
A 1.0 L double-walled reactor, provided with baffles, condenser, top stirrer, thermometer and dropping funnel equipped with a nitrogen inlet was charged with ALIQUAT 336 (4.0 g, 10 mmol), 4-bromo-2-methyl-2-butene (30.0 g, 0.20 mol) and freshly cracked cyclopentadiene (6.6 g, 0.10 mol). A 50 wt. % NaOH aqueous solution (84 g) was then added via the dropping funnel to the turbulently stirred reaction mixture. The reaction mixture was cooled with water during the addition of the base. After 5.5 hours of stirring at room temperature, the stirring was stopped, the layers separated and the product was distilled at reduced pressure. After vacuum distillation, 3.4 g of di-(3-methyl-2-butenyl)-cyclopentadiene were obtained. Characterizaton of the product took place with the aid of GC, GC-MS, $^{13}$C- and $^1$H-NMR.

Example XX
Preparation of di-(3-cyclohexenyl)cyclopentadiene
A 1.0 L double-walled reactor, provided with baffles, condenser, top stirrer, thermometer and dropping funnel equipped with a nitrogen inlet was charged with ALIQUAT 336 (7.6 g, 19 mmol), 3-bromocyclohexene (58.8 g, 0.37 mol) and freshly cracked cyclopentadiene (11.9 g, 0.18 mol). A 50 wt. % NaOH aqueous solution (152 g) was then added via the dropping funnel to the, turbulently stirred reaction mixture. The reaction mixture was cooled with water during the addition of the base. After 4 hours of stirring at room temperature, stirring was stopped and the phases separated, the aqueous basic solution was isolated and removed. GC analysis showed that 4 % of mono- and 96% of di-(3-cyclohexenyl)cyclopentadiene were present in the mixture. The product was distilled at reduced pressure and after vacuum distillation, 36.0 g of di-(3-cyclohexenyl)cyclopentadiene were obtained. Characterization of the product took place with the aid of GC, GC-MS, $^{13}$C- and $^1$H-NMR.

Example XXI
Preparation of di(benzyl)cyclopentadiene
A 1.0 L double-walled reactor, provided with baffles, condenser, top stirrer, thermometer and dropping funnel equipped with a nitrogen inlet was charged with ALIQUAT 336 (8.1 g, 20 mmol), benzylbromide (62.9 g, 0.37 mol) and freshly cracked cyclopentadiene (11.9 g, 0.18 mol). A 50 wt. % NaOH aqueous solution (149 g) was then added via the dropping funnel to the turbulently stirred reaction mixture. The reaction mixture was cooled with water during the addition of the base. After 0.5 hour, the reaction mixture was heated 40° C. After 4 hours, stirring was stopped and the phases separated, the aqueous basic solution was isolated, removed and replaced with a fresh 50 wt. % NaOH solution (146 g). After 0.5 hours of stirring at 40° C., the stirring was stopped, the layers separated and the product was distilled at reduced pressure. After vacuum distillation, 45.0 g of di-(benzyl)cyclopentadiene were obtained. Characterization of the product took place with the aid of GC, GC-MS, $^{13}$C- and $^1$H-NMR.

Example XXII
Preparation of di(1-phenethyl)cyclopentadiene
A 1.0 L double-walled reactor, provided with baffles, condenser, top stirrer, thermometer and dropping funnel equipped with a nitrogen inlet was charged with ALIQUAT 336 (7.2 g, 18 mmol), 1-bromo-ethylbenzene (68.0 g, 0.37 mol) and freshly cracked cyclopentadiene (11.7 g, 0.18 mol). A 50 wt. % NaOH aqueous solution (144 g) was then added via the dropping funnel to the turbulently stirred reaction mixture. The reaction mixture was cooled with water during the addition of the base. After 3.5 hours, the reaction mixture was heated to 55° C. After 0.5 hours of stirring at 55° C., the stirring was stopped, the layers separated and the product was distilled at reduced pressure. After vacuum distillation, 44.4 g of di(1-phenethyl)cyclopentadiene were obtained. Characterization of the product took place with the aid of GC, GC-MS, $^{13}$C- and $^1$H-NMR.

Example XXIII
Preparation of di(2-phenethyl)cyclopentadiene
A 1.0 L double-walled reactor, provided with baffles, condenser, top stirrer, thermometer and dropping funnel equipped with a nitrogen inlet was charged with ALIQUAT 336 (7.0 g, 17 mmol), 2-bromo-ethylbenzene (67.4 g, 0.36 mol) and freshly cracked cyclopentadiene (11.9 g, 0.18 mol). A 50 wt. % NaOH aqueous solution (142 g) was then added via the dropping funnel to the turbulently stirred reaction mixture. The reaction mixture was cooled with water during the addition of the base. After 0.5 hours, the reaction mixture was heated to 55° C. After 6 hours, stirring was stopped and the phases separated, the aqueous basic solution was isolated and removed. GC analysis showed that 3% of mono- and 97% of di-(2-phenethyl)cyclopentadiene were present in the mixture. The product was distilled at reduced pressure and after vacuum distillation, 46.4 g of di-(2-phenethyl)cyclopentadiene were obtained. Characterization of the product took place with the aid of GC, GC-MS, $^{13}$C- and $^1$H-NMR.

Example XXIV
Preparation of di(isopropyl)(cyclohexyl)cyclopentadiene
A 1.0 L double-walled reactor, provided with baffles, condenser, top stirrer, thermometer and dropping funnel equipped with a nitrogen inlet was charged with ALIQUAT 336 (40.6 g, 0.1 mol), cyclohexylbromide (166.2 g, 1.02 mol) and freshly cracked cyclopentadiene (65.9 g, 0.99 mol). A 50 wt. % NaOH aqueous solution (802 g) was then added via the dropping funnel to the turbulently stirred reaction mixture. The reaction mixture was cooled with water during the addition of the base. After 2 hours, iso-propylbromide (266.6 g, 2.79 mmol) was added and then after another 2.5 hours, stirring was stopped and the phases separated, the aqueous basic solution was isolated, removed and replaced with a fresh 50 wt. % NaOH solution (774 g). After another 7 hours of stirring at room temperature, the stirring was stopped, the layers separated and the product was distilled at reduced pressure. After vacuum distillation, 150 g of di-(n-propyl)cyclohexylcyclopentadiene were obtained. Characterization of the product took place with the aid of GC, GC-MS, $^{13}$C- and $^1$H-NMR.

What is claimed is:

1. A process for selectively substituting one or more substituents onto a cyclopentadiene ring to thereby increase the number of substituents on the five-member ring, said process comprising the step of:

reacting a compound comprising a cyclopentadiene ring with at least one first substituting compound comprising a first substituting group and a first halide to thereby substitute the first substituting group onto the cyclopentadiene ring whereby a substituted compound comprising a cyclopentadiene ring having an increased number of substituents on the cyclopentadiene ring is obtained, said reacting step occurring in a reaction mixture comprising at least one phase transfer catalyst, an organic phase and a first aqueous phase, and at least one first base in a molar ratio of from about 5 to about 30 to the compound comprising the cyclopentadiene ring, and comprising the at least one first substituting compound in a quantity, expressed in moles, which corresponds to a stoichiometric amount with no more than 10 mol % excess corresponding to the desired multiplicity of substitution on the cyclopentadiene ring.

2. A process according to claim 1, wherein said the molar ratio is from about 6 to about 20.

3. A process according to claim 1, wherein said molar ratio is from about 7 to about 15.

4. A process according to claim 1, wherein said reacting step comprises introducing a stoichiometric amount of the substituting compound relative to the cyclopentadiene ring.

5. A process according to claim 1, wherein the substituting compound is a primary or secondary alkyl halide.

6. A process according to claim 1, wherein the first base is an alkali metal hydroxide.

7. A process according to claim 6, wherein the first base is sodium hydroxide.

8. A process according to claim 1, wherein the first halide is bromide.

9. A process according to claim 1 further comprising isolating and removing the first aqueous phase from the reaction mixture during said step of reacting the cyclopentadiene ring with at least one first substituting compound producing a desired substituted compound comprising a cyclopentadiene ring; and replacing said first aqueous phase with a second aqueous solution containing at least one second base, which can be the same or different from the first base.

10. A process according to claim 1, further comprising the steps of:

isolating and removing the first aqueous phase from the reaction mixture after said step of reacting the cyclopentadiene ring with at least one first substituting compound produces a desired substituted compound comprising a cyclopentadiene ring; and introducing into the reaction mixture both a second substituting compound comprising a second substituting group and a second halide, and a second aqueous phase comprising at least one second base, wherein the second substituting compound and second base can each be the same as or different from the first substituting compound and the first base, respectively.

11. A process according to claim 1 further comprising isolating and removing the first aqueous phase from the reaction mixture after said step of reacting the cyclopentadiene ring with at least one first substituting compound producing a desired substituted compound comprising a cyclopentadiene ring; and introducing into said reaction mixture both a second substituting compound comprising a second substituting group and a second halide, and a second aqueous phase comprising at least one second base, wherein the second substituting compound is different from the first substituting compound and the second base can be the same or different from the first base.

12. A process according to claim 1, wherein said phase transfer catalyst is present in a quantity, based on the amount of the cyclopentadiene compound, of at least 0.05 equivalents.

* * * * *